United States Patent [19]

Nagasaki et al.

[11] Patent Number: 4,821,116

[45] Date of Patent: * Apr. 11, 1989

[54] ENDOSCOPE EQUIPMENT

[75] Inventors: Tatsuo Nagasaki, Musashino; Hiroyoshi Fujimori, Hachioji, both of Japan

[73] Assignee: Olympus Optical Co., Ltd., Tokyo, Japan

[*] Notice: The portion of the term of this patent subsequent to Aug. 12, 2003 has been disclaimed.

[21] Appl. No.: 27,598

[22] Filed: Mar. 18, 1987

Related U.S. Application Data

[62] Division of Ser. No. 656,375, Oct. 1, 1984, Pat. No. 4,653,478.

[30] Foreign Application Priority Data

Sep. 30, 1983 [JP] Japan ................. 58-183281
Oct. 3, 1983 [JP] Japan ................. 58-184683
Oct. 3, 1983 [JP] Japan ................. 58-184695

[51] Int. Cl.$^4$ ............................. H04N 7/18
[52] U.S. Cl. ......................... 358/98; 128/4; 128/6
[58] Field of Search ............ 358/98; 128/4, 6; 362/293; 350/266, 273-276

[56] References Cited

U.S. PATENT DOCUMENTS

| | | | |
|---|---|---|---|
| 4,604,992 | 8/1986 | Sato | 358/98 |
| 4,615,330 | 10/1986 | Nagasaki et al. | 128/4 |
| 4,621,284 | 11/1986 | Nishioka et al. | 358/98 |
| 4,622,584 | 11/1986 | Nagasaki et al. | 358/98 |
| 4,625,236 | 11/1986 | Fujimori et al. | 358/98 |
| 4,631,582 | 12/1986 | Nagasaki et al. | 358/98 |
| 4,638,353 | 1/1987 | Nagasaki et al. | 358/98 |

OTHER PUBLICATIONS

"Miniature Black and White TV Camera for Endoscopy and Other Medical Applications"; Beuri et al; Bio-Medical Engineering; Apr. 1972; vol. 7, No. 3; pp. 116-121.

"The Newest Technique for Liquid Crystals", published by the Industrial Investigating Society in Japan; May 25, 1983; pp. 203-206.

Primary Examiner—James J. Groody
Assistant Examiner—John K. Peng
Attorney, Agent, or Firm—Armstrong, Nikaido, Marmelstein & Kubovcik

[57] ABSTRACT

This invention concerns an endoscope using a line transfer type solid pickup element which is provided with a means to control the light incident upon the light receiving plane of the solid pickup element and accumulates the optical image from the subject during the incident period and reads the accumulated signal charges during the non-incident period. The means to control the incident light consists of the method to switch ON and OFF the light source driving voltage, method to switch ON and OFF the applied voltage of the liquid crystal filter provided in the optical path, method to provide a rotary filter with shielding regions in front of the light source and method to use a strobo light source. Furthermore, in order to display in color, the combination with the R, G and B color filters is used.

5 Claims, 3 Drawing Sheets

ENDOSCOPE EQUIPMENT

This is a division of application Ser. No. 656,375 filed Oct. 1, 1984, now U.S. Pat. No. 4,653,478.

BACKGROUND OF THE INVENTION

This invention concerns an endoscope using a line transfer type solid state image sensing element suitable for miniaturization.

Recently; various kinds of endoscopes using solid state image sensing elements; such as charge coupled devices for the image sensing means; are being proposed.

The endoscopes using the aforementioned solid state image sensing elements have the advantages that it is possible to prevent the quality of pictures from deteriorating due to the breakage of the fibers in endoscope using the image guide made of an optical fiber bundle and that it is easy to record pictures, and it is expected that they will be increasingly used in the future because further miniaturization and improvement of resolving power can be expected, as the integration technology makes progress.

As the solid state image sensing element, the charge coupled device (CCD) having two functions of photoelectric conversion and scanning is widely used. This CCD is roughly divided into a frame transfer type, line a transfer type and a vertical inter-line type.

In the frame transfer type CCD, firstly photoelectric conversion and signal accumulation are made at a light sensing part during a field period and the charges are put in parallel and transferred to and accumulated in an accumulating part during the short time of a vertical blanking period, and the shielded charges in the accumulating part equivalent to 1 scanning line are transferred in the standard scanning method by means of the horizontal register during the horizontal blanking period, and the signals are sequentially read out.

The line transfer type CCD is provided with a vertical output register and reads out the signals by switching the transferred signals per line.

In the vertical inter-line transfer type CCD, the light sensing part and transferring part are paired and arranged in a line in the longitudinal direction.

The line transfer type CCD can be made smaller than other types of CCD, but it has a disadvantage that when charges are transferred for signal reading, the incident light is received and the signal charge corresponding to a different picture element is superimposed and the smear phenomenon (picture becomes indistinct) occurs.

BRIEF SUMMARY OF THE INVENTION

The objective of this invention is to provide an endoscope using the line transfer type solid state image sensing element which can prevent the smear phenomenon and give clear pictures.

Another objective of this invention is to provide an endoscope whose end part can be made small in diameter.

Still another objective of this invention is to provide an endoscope which can be used even in a narrow body cavity part through miniaturization, thus expanding the scope of application of the endoscope.

Other features and benefits of this invention will be made clear by the following explanation.

DETAILED DESCRIPTION OF THE EMBODIMENTS

Figure 1:
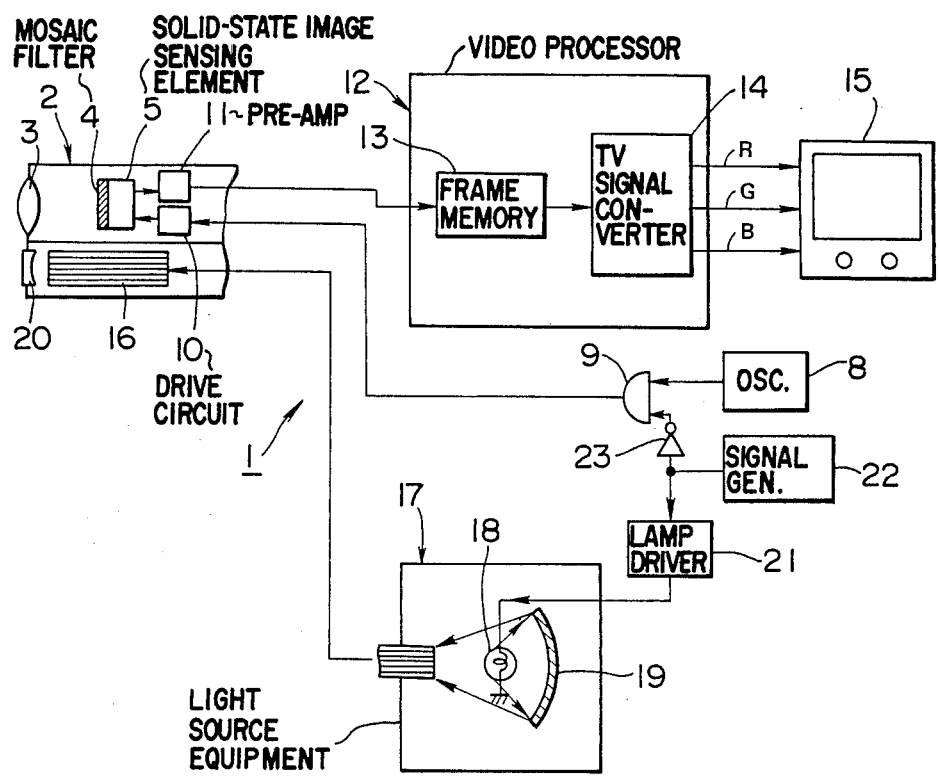
FIG. 1 is a block diagram to show Embodiment 1 of the endoscope related to this invention.
Figure 2:
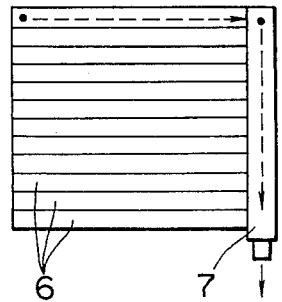
FIG. 2 is a front view to show an approximate makeup of the line transfer type solid state image sensing element.
Figure 3:
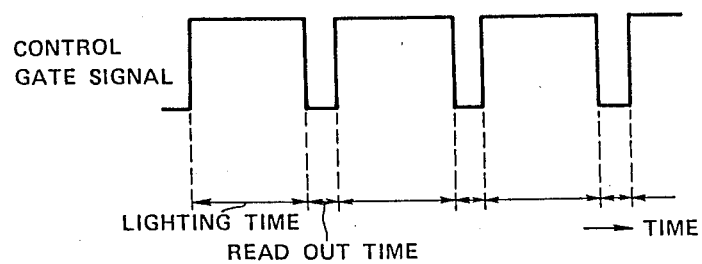
FIG. 3 is an explanatory diagram to show the relationship among the control gate signal, lighting time and readout time in the device in FIG. 1.

FIGS. 1 to 3 concern the first Embodiment of this invention.

As shown in FIG. 1, a hard end component 2 is provided continuously at the front end side of a narrow and flexible inserting member of the endoscope 1 which can be inserted into a body cavity, etc.

The observation window of the said end part 2 is provided with an object lens 3 for image-forming, and at the focal point of the said object lens 3 a line transfer type solid state image sensing element 5 with the tri-color mosaic filter 4 at the front; is provided.

On the image sensing plane of the solid state image sensing element 5, as shown in FIG. 2, the line light sensing part 6 consisting of many light receiving elements arranged in the horizontal direction is formed and the signal charges can be transferred and read from the output register 7 by applying the readout clock signals of the specified phase relationship. The signal charge is output by switching the transfer signal for each line.

The transfer signal to be switched for each line and the readout clock signal of the specified phase relationship are formed by the drive circuit 10 which takes in the reference clock signal output from the oscillator 8 via the AND circuit 9. When the output signal from the drive circuit 10 is applied, the signal read from the solid state image sensing element 5 is amplified in low noise factor by the preamplifier 11, passed through the signal line, and written in the frame memory 13 in the video processor 12.

The signal written in the frame memory 13 is separated and converted into 3 color signals R, G and B on which the horizontal and vertical signals are superposed in the TV signal converter 14 and displayed on the color TV monitor 15. For writing into the frame memory 13, the signals are AD-converted into digital values and after being read out, they are DA-converted into analog values.

In the inserting member a light guide 16 made a flexible optical fiber bundle is inserted for transmitting the illuminating light from a light source to the object. The rear end of the said light guide 16 is attached in a removable way to the light source equipment 17. The illuminating light of the lamp 18 in the light source equipment 17 is reflected by the concave plane of the reflector 19 and condensed and then projected to the rear end face of the light guide 16, and the light is transmitted through the light guide 16 and projected from the front end face fixed in the end part 2 through the light distributing lens 20 to the subject in order for an image can be formed on the image sensing plane by the object lens 3.

The illuminating lamp 18 is driven with the power supplied from the lamp driver 21 and the power supplied to and cut off from the lamp driver 21 is controlled by the control gate signals (shown in FIG. 3) output from the control gate signal generator 22, i.e. when the control gate signal is on a high level, the power is supplied to the illuminating lamp 18 and when low level, the supply is stopped. The above control gate signal is, for example, for high level for 29 msec. and low at 4 msec. (not limited to this).

The above control gate signal is applied to the other input end of the AND circuit 9 via the inverter circuit 23 and only when the level of the signal applied to the input end is high (i.e. control gate signal is at low level), the reference clock signal from the oscillator 8 is output to the drive circuit 10 (i.e. the readout time shown in FIG. 3). That is, the control gate signal generator 22 causes the illuminating lamp 18 to light and to illuminate the subject during the lighting time when the control gate signal is at high level, and the subject image is formed on the image sensing plane face by means of the reflected light from the subject, resolved into the picture element units and received by the light receiving elements and accumulated as charges, and control is made so that the reference clock signal for signal reading is not output to the drive circuit 10, and during the readout time when the control gate signal is at low level, the AND circuit 9 is opened, the reference clock signal is supplied to the drive circuit 10, and the illuminating lamp 18 is extinguished to prevent the light from entering the light receiving elements.

In the first Embodiment thus formed, by means of the control gate signal, the subject is lighted during the lighting time and the reflected light from the subject is received by the light receiving elements and accumulated as charges. During the subsequent readout time when the accumulated charges are sequentially read out by means of the output signal of the drive circuit 10, the illuminating lamp 18 is extinguished to prevent the incident light from being received by the light receiving elements, and therefore, the signals can be read without occurrence of the smear phenomenon.

The read signals are amplified by the preamplifier 11 and written into the frame memory 13 in the video processor 12. During the subsequent lighting time, they are read out sequentially, separated into R, G and B color signals by the sample hold circuit in the TV signal converter 14, superposed on by horizontal and vertical synchronizing signals, applied to the RGB terminals in the color TV monitor 15, to display the subject in color.

The above first Embodiment can make it possible to make small the outside diameter of the end part 2 to contain the solid state image sensing element 5 because it uses a line transfer type solid state image sensing element 5 with small area which is not provided with the transfer part to accumulate the charges received by the light receiving elements forming the light sensing part 6 as well as preventing the smear phenomenon.

The tri-color filter in the first Embodiment is not limited to the color mosaic filter 4, and for example, 3 primary color filters arranged in stripes may be also used.

Figure 1A:
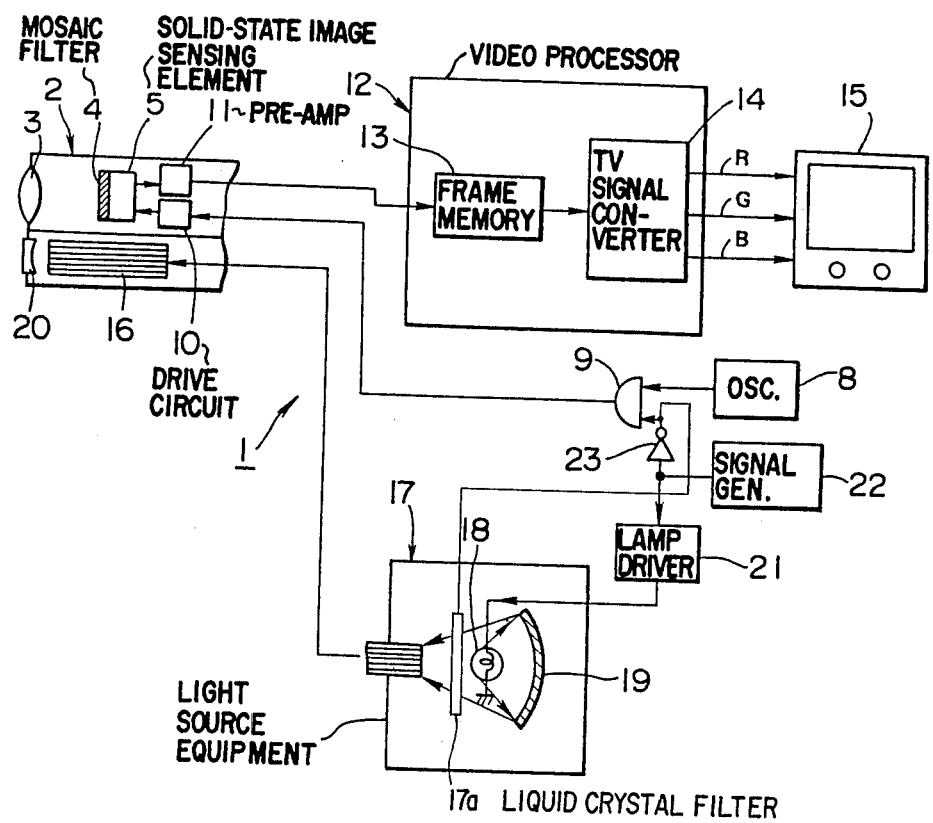
FIG. 1A is a block diagram illustrating another embodiment of the invention.

In the above embodiments, the illuminating lamp 18, is extinguished during the signal readout period so that the light will not be received by the light receiving elements during this period. However this invention is not limited to this, and for example, a liquid crystal filter 17a (as seen in FIG. 1A) can be provided between the rear end face of the light guide 16 and the light source such as the illuminating lamp 18 thus controlling the application of voltage to the liquid crystal filter.

The above liquid crystal filter is not limited to the installation in the light source equipment 19, and the same function can be obtained by providing it between the light distributing lens 20 and the front end face of the light guide 16 (or a light source such as illuminous diode), for example, at the pupil position of the distributing lens 20.

Furthermore, the above liquid crystal filter can be provided in front of the image sensing plane or at the pupil position of the object lens 3 and control can be made so that the light is not received by the light receiving elements during the signal readout time (although illuminated). The important thing is that the light is not received by the light receiving elements of the light sensor 6 of the line transfer type solid state image sensing element during the signal readout time.

We claim:

1. An endoscope, comprising:
    an inserting member having an end component
    a light source means for projecting light through said inserting member onto a subject;
    a line transfer type solid state image sensing means disposed in said end component for receiving an optical image of the subject illuminated by said light source means, and for converting said received image into electrical signals;
    a light control means for controlling the light incident on said solid state image sensing means so that a signal charge is accumulated in said solid state image sensing means during an incident period when reflected light is incident on said solid state image sensing means and light from said light source means is controlled in such a manner that it is not incident on said image sensing means when said signal charge is being read out from said image sensing means, said light control means including,
    (a) a liquid crystal filter means positioned in the light path between said light source means and said solid-state image sensing means for interrupting the light from said light source means incident on said solid-state image sensing means, and
    (b) a circuit means for electrically controlling said liquid crystal filter means such that said light from said light source means is not incident on said image sensing means when said signal charge is being read out from said image sensing means; and
    a monitor means for displaying the subject image on the basis of the electrical signal read out from said solid-state image sensing means.

2. The endoscope of claim 1, wherein said liquid crystal filter means is disposed between said light source means and a light guide for directing light from said light source means onto the subject.

3. An endoscope, comprising:
    an inserting member having an end component;
    a light source means for projecting light through said inserting member onto a subject;
    a line transfer type solid-state image sensing means disposed in said end component for receiving an optical image of the subject illuminated by solid light source means, and for converting said received image into electrical signals, and
    wherein said image sensing means has one of a mosaic filter and a color stripe filter on the image sensing surface thereof for receiving a color image of said subject illuminated by white light;

a light controlling means for controlling light incident on said solid-state image sensing means so that a signal charge is accumulated in said image sensing means during an incident period when reflected light is incident on said image sensing means and light from said light source means is controlled in such a manner that it is not incident on said image sensing means when said signal charge is being read out from said image sensing means; and a monitor means for displaying in color, the subject image on the basis of electrical signals read out from said solid-state image sensing means.

4. An endoscope, comprising:

an inserting member having an end component;

a light source means for projecting light through said inserting member onto a subject;

a line transfer type solid-state image sensing means disposed in said end component for receiving an optical image of the subject illuminated by the light source, and for converting said received image into electrical signals;

a light controlling means for controlling light incident on said solid-state image sensing means so that a signal charge is accumulated in said solid-state image sensing means during an incident period when reflected light is incident on said image sensing means and light from said light source means is controlled in such a manner that it is not incident on said image sensing means when said signal charge is being read out from said image sensing means; and a monitor means for displaying the subject image on the basis of electrical signals read out from said solid-state image sensing means.

5. An endoscope, comprising:

an inserting member having an end component;

a light source means for projecting light through said inserting member onto a subject;

a line transfer type solid-state image sensing means disposed in said end component for receiving an optical image of the subject illuminated by the light source, and for converting said received image into electrical signals;

a light controlling means for controlling light incident on said solid-state image sensing means so that a signal charge is accumulated in said solid-state sensing means during an incident period when reflected light is incident on said image sensing means, said light controlling means including a circuit means for electrically controlling said light source means such that said light source means is turned off when said signal charge is being read out from said image sensing means; and a monitor means for displaying the subject image on the basis of the electrical signal read out from said solid-state image sensing means.

* * * * *